United States Patent [19]

Heimke et al.

[11] 4,304,553
[45] Dec. 8, 1981

[54] DENTAL IMPLANT FORMED OF AL₂O₃-CERAMIC FOR FASTENING A SUPERSTRUCTURE

[75] Inventors: Günther Heimke, Mannheim; Reinhold Fritz, Stuttgart, both of Fed. Rep. of Germany

[73] Assignee: Friedrichsfeld GmbH, Mannheim, Fed. Rep. of Germany

[21] Appl. No.: 737,579

[22] Filed: Nov. 1, 1976

[30] Foreign Application Priority Data

Nov. 3, 1975 [DE] Fed. Rep. of Germany ....... 2549114

[51] Int. Cl.³ .............................................. A61C 8/00
[52] U.S. Cl. .................................... 433/173; 433/201
[58] Field of Search ...................... 32/10 A; 128/92 C

[56] References Cited

U.S. PATENT DOCUMENTS

| 2,857,670 | 10/1958 | Kiernan, Jr. | 32/10 A |
| 3,797,113 | 3/1974 | Brainin | 32/10 A |
| 3,818,512 | 6/1974 | Shersher | 128/92 C |
| 3,827,145 | 8/1974 | Richards | 32/10 A |
| 3,837,009 | 9/1974 | Walker | 128/92 C |

FOREIGN PATENT DOCUMENTS

| 1030690 | 12/1950 | France | 32/10 A |
| 1083769 | 9/1967 | United Kingdom | 32/10 A |
| 1305478 | 1/1973 | United Kingdom | 32/10 A |

Primary Examiner—Gene Mancene
Assistant Examiner—John J. Wilson
Attorney, Agent, or Firm—Herbert L. Lerner

[57] ABSTRACT

A superstructure-fastening dental implant formed of Al₂O₃-ceramic material having a distal end and a proximal end opposite to the distal end thereof and including a cylindrical shaft formed with constrictions at least partly defined by annular surfaces formed on the shaft, the annular surfaces extending perpendicularly to the axis and facing toward the proximal end of the dental implant, and means including a threaded bushing for anchoring a superstructure at the distal end of the dental implant, the proximal end of the dental implant being rounded and in the form of a spherical calotte having a smooth and uninterrupted surface.

5 Claims, 1 Drawing Figure

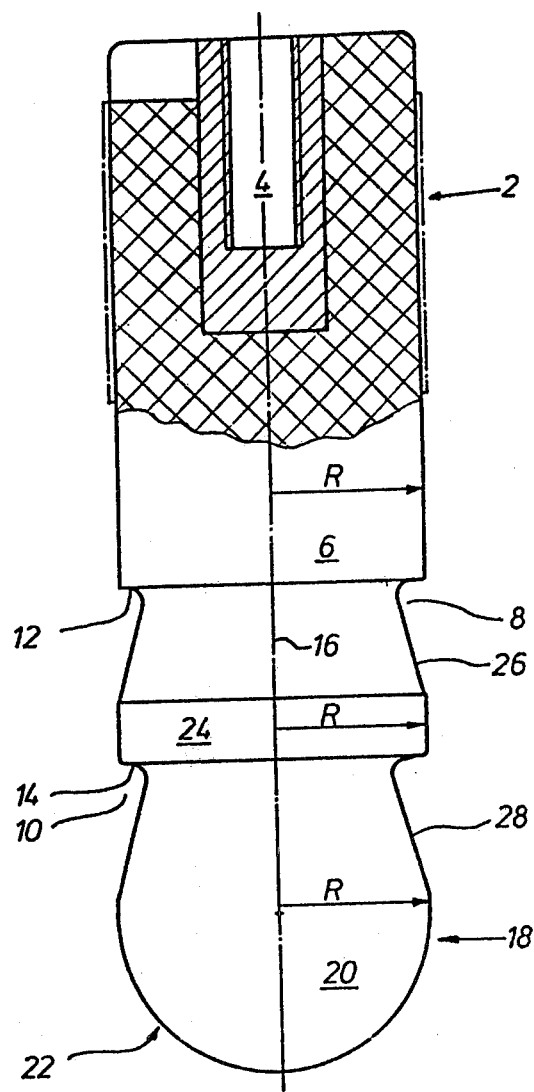

DENTAL IMPLANT FORMED OF AL$_2$O$_3$-CERAMIC FOR FASTENING A SUPERSTRUCTURE

The invention relates to a dental implant formed of Al$_2$O$_3$-ceramic material for fastening a superstructure and, more particularly, to such a dental implant having means for anchoring the superstructure at a distal end of the dental implant and wherein the dental implant has a cylindrical shaft formed with constrictions defined by surfaces extending substantially perpendicularly to the axis of the dental implant, the dental implant also having a proximal end that is rounded.

A ceramic dental implant of the foregoing general type has become known heretofore from "Neue Aspekte der Implantologie" (New Aspects of Implantology) by Samuel Sandhaus, published by MedicaVerlag, and especially pages 156 to 163 thereof. This heretofore known dental implant formed of Al$_2$O$_3$-ceramic is screwed into the maxillary or jaw bone, it being suitably formed in all of the parts thereof to perform that function. The distal end of the known dental implant is hexagonal to permit the dental implant to be screwed into the maxillary bone with a screw spanner. The surfaces extending substantially perpendicularly to the axis of the dental implant form screw surfaces that are oriented or face toward the distal end of the dental implant. The proximal end of the heretofore known dental implant is conically constructed to displace or dislodge the bone as dental implant is being screwed into the maxillary bone and is formed with a slot into which bone material is supposed to grow and prevent subsequent unscrewing and loosening of the dental implant.

This heretofore known dental implant has taken into account the prerequisite of the screw-fastening thereof but not, however, those requirements which must be fulfilled so that the bone formation and bone preservation or maintenance in vicinity of the implant is optimally promoted.

It is accordingly an object of the invention to provide a dental implant formed of Al$_2$O$_3$-ceramic for fastening a superstructure which avoids the foregoing disadvantages of the heretofore known dental implant of this general type and which, more specifically, does optimally promote bone formation and bone preservation and maintenance in vicinity of the implant.

With the foregoing and other objects in view, there is provided, in accordance with the invention, a superstructure-fastening dental implant formed of Al$_2$O$_3$-ceramic material having a distal end and a proximal end opposite to the distal end thereof and comprising a cylindrical shaft formed with constrictions at least partly defined by annular surfaces formed on the shaft, the annular surfaces extending perpendicularly (in fact, exactly perpendicularly in a preferred embodiment) to the axis and facing toward the proximal end of the dental implant and means comprising a threaded bushing for anchoring a superstructure at the distal end of the dental implant, the proximal end of the dental implant being rounded and in the form of a spherical calotte having a smooth and uninterrupted surface.

In order to preserve the bone as much as possible and to stimulate bone formation in vicinity of the implant, the chewing force must be transmitted in the same direction to the bone as is the case with natural teeth. Natural teeth are oriented essentially perpendicularly to the maxillary bone. Since the maxillary bone is slightly curved in the tooth-carrying region thereof, the teeth in the rear part of the jaw are also not disposed in the same direction as in the forward part of the jaw. Dental implants must be oriented likewise; this is not possible with the heretofore known dental implants because the superstructure must be stuck onto fastenings constructed as hexagonal heads which, for this reason, must all have an exactly parallel orientation. With the construction of the invention, on the other hand, the anchoring means at the distal end of the dental implant is constructed as a threaded bushing so that it is possible for the dental technician to form bores in the superstructure in such a manner that, by means of these bores, a screw-connection thereof with the dental implant is possible at any desired angles. As an essential prerequisite for attaining the objective of the invention of the instant application, assurance is provided initially by the threaded bushing for a correct orientation at the distal end of the dental implant. Furthermore, the feature of the surfaces at least partly defining the constrictions being oriented or facing toward the proximal end rather than the distal end of the dental implant serves to permit transmission of the chewing force to the tissue growing into the constrictions and to stimulate bone formation. In contrast thereto, in the heretofore known dental implants, the surfaces defining the constrictions must be oriented toward or face the distal end of the known dental implants in order to serve as screw surfaces for driving the known dental implant into the bone.

In order to prevent the unscrewing and consequent loosening of the heretofore known dental implant, the latter has been provided with a slot at the bottom thereof into which bone material grows. However, this ingrowing of bone material prevents the formation of collagen fibers tangentially oriented to the surface which, considered three-dimensionally, form a hammock-like structure and resiliently support the implant. In accordance with the invention, therefore, the proximal end of the dental implant is constructed as a spherical calotte having a smooth and uninterrupted surface; this promotes the formation of the callagen fibers, which are suspended from a bone tuberosity or bulge, the formation of which is stimulated by the annular surfaces adjacent the proximal end of the dental implant of the invention, oriented to or facing the proximal end and extending perpendicularly to (preferably exactly perpendicularly to) the axis of the dental implant.

The formation of hammock-like disposed collagen fibers produced by means of the smooth spherical calotte is thus permitted on the one hand, due to the disposition of the dental implant perpendicularly to the maxillary bone (permitted due to the threaded bushing of the invention), as well as, on the other hand, due to the annular surface of the constriction which is oriented toward or faces the proximal end of the dental implant and stimulates the formation of an annular tuberosity or bulge. In their combination, therefore, all of the foregoing features of the invention, cooperate to provide the purpose or objective of the invention in common.

In accordance with another feature of the invention, the dental implant is of unipartite construction.

In accordance with a further feature of the invention, the constrictions are two in number, one of which is closer to the proximal end of the dental implant and is connected to the spherical calotte, the cylindrical shaft including a first cylindrical portion located between the other of the constriction and the distal end of the dental implant and a second cylindrical portion located between the two constrictions, both the first and second cylindrical portions and the spherical calotte having the same diameter.

In accordance with an added feature of the invention, the shaft has a portion thereof formed with a transition surface partly defining and extending from the other of the constrictions to the second cylindrical portion, the transition surface conically widening in direction toward the proximal end of the dental implant and forming a vertex angle of 30°.

In accordance with a concomitant feature of the invention, the shaft has a portion thereof formed with a transition surface partly defining and extending from the one of the constrictions, to the spherical calotte, the transition surface conically widening in direction toward the proximal end of the dental implant and forming a vertex angle of 30°.

Other features which are considered as characteristic for the invention are set forth in the appended claims.

Although the invention is illustrated and described herein as embodied in a dental implant formed of aluminum oxide ($Al_2O_3$) ceramic for fastening a superstructure, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying single FIGURE of the drawing which is a longitudinal view, partly in cross section, of a cylindrical unipartite dental implant constructed in accordance with the invention.

Referring now to the FIGURE of the drawing, there is shown therein a dental implant according to the invention, having a distal end 2, located at the top of the figure, carrying a threaded bushing 4 formed of gold and/or platinum serving as means for anchoring a superstructure. The dental implant is formed with a cylindrical shaft 6 having two annular constrictions 8 and 10 which are bounded by annular surfaces 12 and 14 at the sides thereof facing toward the distal end 2. The annular surfaces 12 and 14 extend perpendicularly to the axis 16 of the dental implant and are oriented more closely toward the proximal end 18, located at the bottom of the figure, than the distal end 2 of the implant. A spherical calotte 20 is connected to the constriction 10 located closer to the proximal end 18 and has a completely smooth hemispherical surface 22 and no cracks or unevennesses into which bone material could grow.

The cylindrical part of the shaft 6 has a radius R. Directly above the annular surface 14, as viewed in the FIGURE, a similarly cylindrical section 24 has the same radius R. The transition from the upper constriction 8, as viewed in the FIGURE, to the cylindrical section 24 forms a conical surface 26 which, with the axis 16, includes an angle of 15°, thereby forming a cone vertex angle of 30°.

The diameter of the spherical calotte 20 is likewise equal to the diameter 2R of the cylindrical sections 6 and 24. The transition surfaces from the constriction 10 to the spherical calotte 20 is also formed by a conical surface 28 extending toward the proximal end 18 and having a vertex angle also of 30°.

The dental implant according to the invention is capable of being produced very readily of dense $AL_2O_3$ ceramic in a lathe since it is axially symmetrical in all parts thereof and has no milled portions or recesses formed therein. The bushing 4 formed of gold or platinum or both can be pasted in above.

To introduce or insert the dental implant, an artificial alveolus is bored into the maxillary bone and in fact substantially perpendicularly to the surface of the maxillary bone, in accordance with the ideal natural orientation of the teeth to the respective location. The selection of this orientation can be made independently of the construction of the superstructure.

Bone-forming tissue grows into the constrictions 8 and 10 and, in the region of the spherical surface 22 of the spherical calotte 20, the bone is transformed in a thin layer into soft connective tissue. During chewing movements, a chewing force is exerted in direction of the axis 16. Because of the flexibility or yieldingness of the connective tissue in the region of the spherical surface 22, the chewing force also presses against the new tissue that has grown into the constrictions 8 and 10 and stimulates or activates it to ossification. An annular bone bulge or tuberosity is formed in the region of the lower constriction 10, as viewed in the FIGURE, and collagen fibers, which engage the spherical surface 22 and resiliently carry the spherical calotte 20, grow onto the annular bone tuberosity.

The dental implant according to the invention is consequently relatively easily manufacturable and stimulates the surrounding tissue to form collagen fibers and neoplasmic bone, whereby assurance that the dental implant is reliably ingrown in the maxillary bone is provided and regression of the bone tissue is prevented due to the chewing force acting upon the bone.

There are claimed:

1. A superstructure-fastening dental implant
   (a) formed of $Al_2O_3$-ceramic material having a distal end and a proximal end opposite to the distal end thereof and comprising
   (b) a cylindrical shaft formed with constrictions at least partly defined by annular surfaces formed on said shaft,
   (c) said annular surfaces extending perpendicularly to the axis and facing only toward the proximal end of the dental implant,
   (d) and means comprising a threaded bushing for anchoring a superstructure at the distal end of the dental implant,
   (e) The proximal end of the dental implant being rounded and in the form of a spherical calotte having a smooth and uninterrupted surface anchorable in bone,
   (f) said cylindrical shaft being formed with respective conical surfaces tapering in axial direction toward said distal end and away from said spherical calotte and down toward said constrictions.

2. Dental implant according to claim 1 wherein said constrictions are two in number, one of which is closer to the proximal end of the dental implant and is connected to said spherical calotte, said cylindrical shaft including a first cylindrical portion located between the other of said constrictions and the distal end of the dental implant and a second cylindrical portion located between said two constrictions, both said first and second cylindrical portions and said spherical calotte having the same diameter.

3. Dental implant according to claim 2 wherein one of said conical surfaces partly defines and extends from said other of said constrictions to said second cylindrical portion, said one conical surface widening in direction toward the proximal end of the dental implant and forming a vertex angle of 30°.

4. Dental implant according to claim 2 wherein another of said conical surfaces partly defines and extends from said one of said constrictions to said spherical calotte, said other conical surface widening in direction toward the proximal end of the dental implant and forming a vertex angle of 30°.

5. Dental implant according to claim 2 wherein said shaft has a portion thereof formed with two of said conical surfaces, one conical surface thereof partly defining and extending from said other of said constrictions to said second cylindrical portion, and the other conical surface thereof partly defining and extending from said one of said constrictions to said spherical calotte, both said conical surfaces widening in direction toward the proximal end of the dental implant and forming respective vertex angles of 30°.

* * * * *